United States Patent [19]

Kraus et al.

[11] 4,360,480

[45] * Nov. 23, 1982

[54] AROMATIC DIAMINO PHOSPHORAMIDES, THIOPHOSPHORAMIDES AND PHOSPHORAMIDATES

[75] Inventors: Menahem A. Kraus; Moshe A. Frommer, both of Rehovot; Mara Nemas, Neve Monoson; Rodika Gutman, Kiryat Sharet, all of Israel

[73] Assignee: A.T. Ramot Plastics Ltd., Tel-Aviv, Israel

[ * ] Notice: The portion of the term of this patent subsequent to Nov. 11, 1997, has been disclaimed.

[21] Appl. No.: 155,837

[22] Filed: Jun. 2, 1980

Related U.S. Application Data

[63] Continuation-in-part of Ser. No. 652,812, Jan. 27, 1976.

[30] Foreign Application Priority Data

Jan. 27, 1975 [IL]  Israel ........................................ 46510
Jul. 15, 1975 [IL]  Israel ........................................ 47709

[51] Int. Cl.$^3$ ........................................ C08G 69/42
[52] U.S. Cl. ................................ 260/944; 210/500.2
[58] Field of Search ............................ 564/12, 14, 15; 210/500 M; 528/393, 337, 391; 260/944

[56] References Cited

U.S. PATENT DOCUMENTS 3,531,550  9/1970  Herber et al. ..................... 564/14 X
4,233,434  11/1980  Kraus et al. ......................... 528/337

Primary Examiner—Frank A. Spear, Jr.
Attorney, Agent, or Firm—Browdy and Neimark

[57] ABSTRACT

The present invention relates to novel aromatic diamino phosphoramides, thiophosphoramides and phosphoramidates and to a process for the production of same.

12 Claims, No Drawings

AROMATIC DIAMINO PHOSPHORAMIDES, THIOPHOSPHORAMIDES AND PHOSPHORAMIDATES

RELATION TO OTHER APPLICATIONS

The present application is a continuation-in-part application of U.S. patent application Ser. No. 652,812, filed Jan. 27, 1976, the entire contents of which are hereby incorporated by reference.

Another continuation-in-part application is Ser. No. 904,286, filed May 9, 1978, now U.S. Pat. No. 4,233,434.

STATE OF THE PRIOR ART

Various phosphorus-containing compounds are being used as insecticides, medications, monomers and additives for polymers. Only few aromatic diamino phosphoric acids derivatives have been reported previously. One phosphonic acid derivative was prepared as follows:

$$C_6H_5\text{---}POCl_2 + NH_2\text{---}m\text{---}C_6H_4\,NH_2$$
$$C_6H_5\text{---}PO\text{---}(NH\text{---}m\text{---}C_6H_4\,NH_2)_2$$

(E. Bloecker and E. Eckhardt, Gen. Offen. No. 2,062,774, 13.7.1972)

The compound seems not to have been isolated and characterized but was used directly in polymerization.

Aromatic diamino phosphoramides and phosphoramidates are potentially useful in any of the above uses and especially as monomers and polymer additives.

SUMMARY OF THE INVENTION

The present invention relates to novel compounds of the general formula $$NH_2\quad QY\quad \overset{\overset{X}{|}}{\underset{\underset{Z}{\|}}{P}}\quad Y\quad Q\quad NH_2$$

wherein
X designates NH Ar', N(R)Ar', NRR', OR, O Ar', SR
Y designates —O—, —NH—, —S—, —N(CH$_3$)—
Z designates =O or =S
Q is Ar or aralkylene
Ar designates p—C$_6$H$_4$, m—C$_6$H$_4$, R"C$_6$H$_3$.

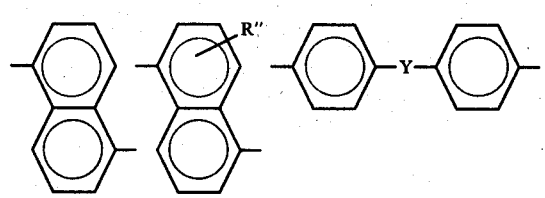

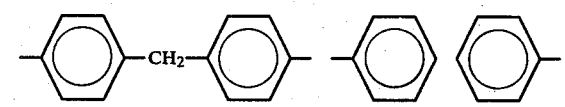

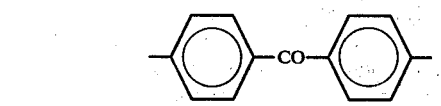

Ar' designates C$_6$H$_5$, R'C$_6$H$_4$
R and R' designate CH$_3$, C$_2$H$_5$, n—C$_3$H$_7$
R" designates CH$_3$, C$_2$H$_5$, n—C$_3$H$_7$, OCH$_3$, OH, COOH or COOR,
a process for preparing such compounds and products prepared from such compounds.

The present invention further relates to a process for producing compounds of Formula I, defined above, which process comprises reacting a phosphorus oxyhalide of the formula Z=P(hal)$_3$, wherein hal designates chlorine or bromine, with a nucleophile selected from amines, alcohols and phenols in the presence of a base, to give a compound of the formula $$\overset{\overset{X}{|}}{\underset{\underset{Z}{\|}}{P}}\text{(hal)}_2$$

where hal is as defined above, which compound is reacted with a nitroaromatic nucleophile HYQNO$_2$ in the presence of a base to yield a dinitro condensation product X—P(——Y—Q—NO$_2$)$_2$, and hydrogenating same to give the desired product, wherein X,Y,Z and Q are as defined with respect of the product of Formula (I). Preferred nucleophiles for the first stage of the reaction are aniline, lower alkanols such as methanol, ethanol and the like, and phenol. Preferred nitroaromatic compounds are nitroaniline, nitrophenol, nitrobenzylamine. The hydrogenation is preferably carried out by means of hydrogen on a suitable palladium catalyst.

The novel compounds are prepared according to the following reaction scheme:

Scheme I

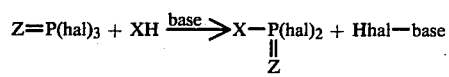

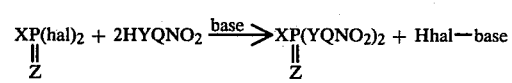

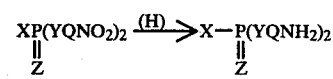

wherein hal designates a halogen selected from chlorine and bromine; X, Y and Z are as defined above.

In reaction 1 a phosphorus oxyhalide or thiohalide is treated with a nucleophile in the presence of an acid acceptor. The dihalide obtained is treated in reaction 2 with a nitroaromatic or araliphatic nucleophile. The dinitro compound obtained is reduced in reaction 3 to the corresponding diamine by a chemical reagent or catalytic hydrogenation.

Suitable oxyhalides are phosphoryl chloride and phosphoryl bromide. A suitable phosphorus thiohalide is thiophosphoryl chloride.

Suitable nucleophiles for reaction 1 are amines such as for example aniline, naphthylamine, alkylamines; alcohols such as methanol, ethanol, propanol, butanol; phenolic compounds such as phenol, p-dimethylamino-phenol, p-methoxyphenol, naphthol; thiols such as thioalkanes.

Suitable nitroaromatic nucleophiles for reaction 2, are for example nitroanilines, nitrophenols, nitrobenzylamines, nitrobenzyl alcohols.

According to a preferred embodiment of the invention the reaction between the oxyhalide or thiohalide and the nucleophile is effected at a ratio of 1:2 up to 1:4 at a temperature of 0° to about 80°.

Reaction 2 between the phosphoric dihalide and the nitroaromatic nucleophile is effected at 10° to about 110° C. with or without an acid acceptor such as pyridine.

As a specific example of general Scheme 1 the preparation of 3,3'-diamino-N,N', N"-triphenylphosphoric triamide is described in Scheme II.

Scheme II

1. $POCl_3 + 2\ C_6H_5\ NH_2 \rightarrow C_6H_5\ NHPO\ Cl_2 + C_6H_5\ NH_3^+\ Cl^-$
2. $C_6H_5\ NH\ POCl_2 + 2\ NH_2\text{—m—}C_6H_4\ NO_2 \rightarrow C_6H_5\ NH\ PO\ (NH\text{—m—}C_6H_4\ NO_2)_2$

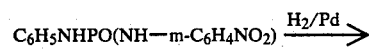

3.

$C_6H_5NHPO(NH\text{-m-}C_6H_4NH_2)_2$

Many of the title compounds are crystalline solids with melting points in the range of 150°–220° C. They are normally highly reactive, light-sensitive compounds and should be prepared, handled and stored with care.

The compounds may be used in the preparation of poly(phosphoramides) and poly(phosphoramidates) as described in U.S. Pat. No. 4,233,434. Also, they can be used as comonomers for polyamides, polyurethanes, polycarbonates. They are also potentially useful as starting materials for insecticides, medications and other products.

DESCRIPTION OF THE PREFERRED EMBODIMENT

The invention is illustrated with reference to the following Examples, which are to be construed in a non-limitative manner.

EXAMPLE 1

Preparation of compound

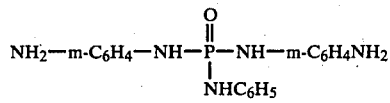

Phosphorus oxychloride is treated with 2 equivalents of aniline in benzene at room temperature. The product N-phenyl phosphoramide dichloride, crystallizes upon partial evaporation of the solvent. Condensation of this product with m-nitroaniline is carried out in pyridine at 60° C. The product, 3,3-dinitro-N,N', N"-triphenylphosphoric triamide is precipitated in an HCl-ice mixture and is recrystallized from ethanol-water.

mp. - 209°–210°. Calculated: C=52.30%. H=3.87%. Found: C=52.69%. H=4.82%.

The dinitro compound is hydrogenated at 4 atm over Pd/C. The product is 3,3'-diamino-N,N', N"-triphenylphosphoric triamide.

mp. 208°–209°. Calculated: C=61.18%. H=5.71%. Found: C=61.05%. H=5.77%.

EXAMPLE 2

Preparation of compound

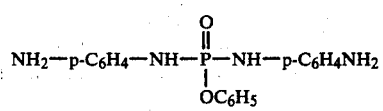

Phenyl phosphate dichloride,

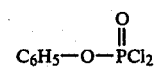

is obtained by the reaction of phenol with phosphorus oxychloride. It is condensed with 2 equivalents of p-nitroaniline as in Ex. 1. Reduction of the condensation product is accomplished by catalytic hydrogenation. The diamine obtained has elemental analysis as follows:

Calculated: C=61.01%, H=5.40%. Found: C=61.15%. H=5.50%.

EXAMPLE 3

Synthesis of Compound

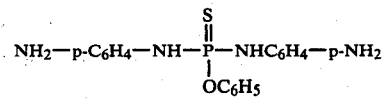

Phenol is treated with excess thiophosphoryl chloride (at reflux) to yield $C_6H_5\ PS\ Cl_2$. This product is condensed with p-nitroaniline and hydrogenated as set out in Example 1.

EXAMPLE 4

Preparation of Compound

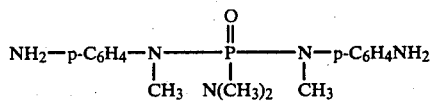

Dimethylaminophosphoryl dichloride is obtained by reaction of phosphorus oxychloride and dimethylaniline hydrochloride. The condensation with p-nitroaniline is carried out as in Example 1. The dinitro product,

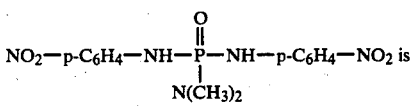

is permethylated by a phase transfer reaction. To the triamide in dioxane is added excess methyl iodide and an aqueous solution of 50% (5/5) of NaOH and 0.3 equivalents of tetrabutylammonium bromide. The N,N'-methylated compound is obtained by vigorous stirring and heating at 40° C. Hydrogenation yields the title compound.

EXAMPLE 5

Preparation of Compound

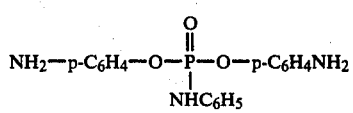

N-phenyl phosphoric amide dichloride is treated at 80° C. during 6 hrs with excess p-nitrophenol in pyridine. The product is hydrogenated as in Example 1 to yield the title compound.

EXAMPLE 6

Synthesis of Compound

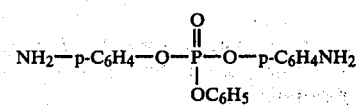

Phenyl phosphate dichloride (see Ex. 2) is treated at 60° C. during 12 hrs with excess p-nitrophenol. Hydrogenation of the product yields the title compound.

EXAMPLE 7

Preparation of Compound

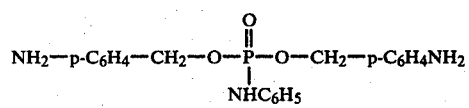

N-phenyl phosphoramide dichloride is condensed with p-nitrobenzyl alcohol and the product hydrogenated essentially as set out in Example 1.

EXAMPLE 8

Preparation of Compound

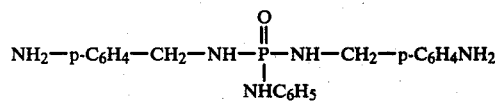

N-phenyl phosphoramide dichloride is condensed with p-nitrobenzylamine and the product hydrogenated essentially as set out in Example 1.

We claim:

1. A compound of the formula (I)

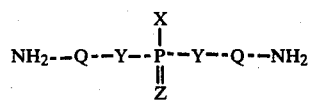

wherein
X designates NH Ar', N(R)Ar', NRR', OR, or OAr'
Y designates —O—, —NH—, —S— or —N(CH$_3$)—
Z designates =O or =S
Q is Ar or aralkylene
Ar designates p—C$_6$H$_4$, m—C$_6$H$_4$, m—C$_6$H$_4$, R'C$_6$H$_3$,

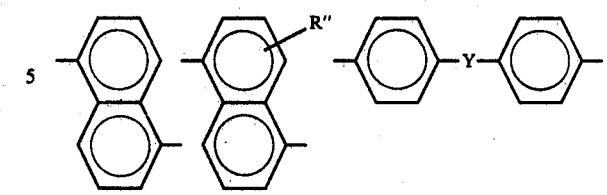

Ar' designates C$_6$H$_5$ or R'C$_6$H$_4$
R and R' designate CH$_3$, C$_2$H$_5$ or n—C$_3$H$_7$
R" designates CH$_3$, C$_2$H$_5$, n—C$_3$H$_7$, OCH$_3$, OH, COOH or COOR 2. A compound according to claim 1, of the Formula

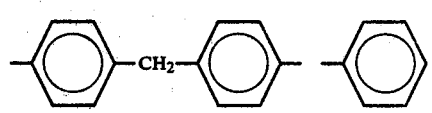

3. A compound according to claim 1, of the Formula

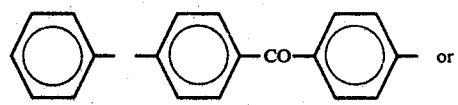

4. A compound according to claim 1, of the Formula

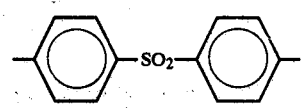

5. A compound according to claim 1, of the Formula

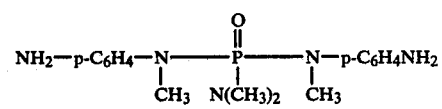

6. A compound according to claim 1, of the Formula

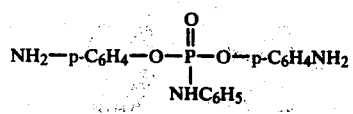

7. A compound according to claim 1, of the Formula

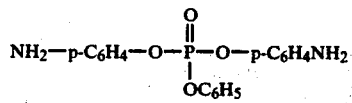

8. A compound according to claim 1, of the Formula

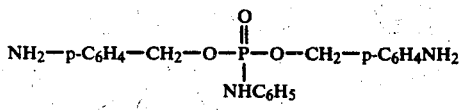

9. A compound according to claim 1, of the Formula

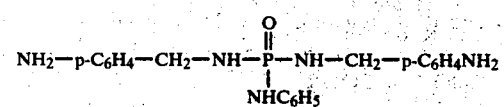

10. A process for the production of compounds of Formula (I) defined in claim 1, which comprises reacting a phosphorus oxyhalide of the formula $Z=P(hal)_3$, wherein hal designates chlorine or bromine, with a nucleophile selected from amines, alcohols and phenols in the presence of a base, to give a compound of the formula

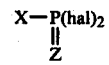

where hal is as defined above, which compound is reacted with a nitroaromatic nucleophile $HYQNO_2$ in the presence of a base to yield a dinitro condensation product

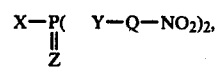

and hydrogenating same to give the desired product, wherein X,Y,Z and Q are as defined with respect to the product of Formula (I).

11. A process according to claim 10, wherein the nucleophile is selected from the group consisting of aniline, lower alkanols and phenol.

12. A process according to claim 10, wherein the nitroaromatic compound is selected from the group consisting of nitroaniline, nitrophenol and nitrobenzylamine.